United States Patent [19]

Borror et al.

[11] 4,139,704
[45] Feb. 13, 1979

[54] CYCLIC AMINO CONTAINING BENZISOTHIAZOLES

[75] Inventors: Alan L. Borror, Lexington; James W. Foley, Andover; John W. Lee, Jr., Harvard, all of Mass.

[73] Assignee: Polaroid Corporation, Cambridge, Mass.

[21] Appl. No.: 836,022

[22] Filed: Sep. 23, 1977

[51] Int. Cl.$^2$ ............................................ C07D 417/10
[52] U.S. Cl. .................................... 544/135; 544/58; 544/368; 260/301; 546/198; 546/205; 546/206; 546/236; 546/192
[58] Field of Search ....................... 544/135, 58, 368; 260/301, 293.57

[56] References Cited

PUBLICATIONS

Fritsch, "Ber". vol. 29 (1896), pp. 2290–2301.
Abramovitch et al., "J. Chem. Soc." Perkin Trans. I., 22 (1974), pp. 2589–2594.
Horli, "Chem. Abstracts", vol. 61 (1964) 12008f and 12008g.

*Primary Examiner*—Natalie Trousof
*Assistant Examiner*—R. W. Ramsuer
*Attorney, Agent, or Firm*—Sybil A. Campbell

[57] ABSTRACT

This invention relates to 3-(phenyl/naphthyl)benz[d]isothiazole-1,1-dioxides wherein the phenyl or naphthyl substituent possesses an N-heterocyclic moiety in the para position. These compounds are useful as intermediates in the synthesis of certain 3,3-disubstituted-2,3-dihydrobenz[d]isothiazole-1,1-dioxide dyes which find utility as, for example, photographic optical filter agents and filter agent precursors.

13 Claims, No Drawings

CYCLIC AMINO CONTAINING BENZISOTHIAZOLES

BACKGROUND OF THE INVENTION

1. Field of the Invention

This invention relates to certain 3-substituted-benz[d]isothiazole-1,1-dioxides, and in particular, it relates to 3-(carbocyclic aryl)-benz[d]isothiazole-1,1-dioxides wherein the carbocyclic aryl group is substituted in the para position with an N-heterocyclic moiety.

2. Description of the Prior Art

Though various 3-substituted-benz[d]isothiazole-1,1-dioxides have been disclosed, only a few 3-aryl derivatives are known. P. Fritsch, Ber., 29, p. 2290 (1896) reported that the 3-phenyl derivative was obtained by the reaction of 3-chlorobenz[d]isothiazole-1,1-dioxide (saccharin pseudo-chloride) and benzene under Friedel-Crafts conditions. The 3-(p-dimethylaminophenyl) derivative was prepared similarly. The 3-(p-chlorophenyl) derivative was obtained by the treatment of ammonium 2-(4'-chlorobenzoyl)benzenesulfonate with phosphorus pentachloride as reported by Z. Horii, Jap. Patents Nos. 10,131/1964 and 8832/1964. R. A. Abramovitch et al, J. Chem. Soc., Perkin Trans. I, 22, p. 2589 (1974) reported that the reaction of alkyl- and aryllithium compounds with 3-oxo-2,3-dihydrobenz[d]isothiazole-1,1-dioxide (saccharin) in tetrahydrofuran at −78° C gave the corresponding 3-alkyl or 3-aryl derivatives exclusively and prepared the 3-phenyl, 3-(o-tolyl), 3-(p-methoxyphenyl) and 3-(2-pyridyl) derivatives in this manner. The latter authors also reported that the 3-phenyl derivative was prepared by the treatment of saccharin with two equivalents of phenylmagnesium bromide in tetrahydrofuran at ambient temperature.

Copending U.S. patent application Ser. No. 836,025 of Alan L. Borror, James W. Foley, Marcis M. Kampe and John W. Lee, Jr. filed concurrently herewith is directed to a method of synthesizing 3,3-disubstituted-2,3-dihydrobenz[d]isothiazole-1,1-dioxides possessing a carbonyl group in the 2-position. Depending upon the carbonyl group and the 3,3 substituents, the products of the synthesis may be employed as pH-sensitive indicator dyes, antihalo dyes or photographic optical filter agents. As disclosed and claimed therein, the method of preparing these compounds comprises reacting a 3-(phenyl/naphthyl)-benz[d]isothiazole-1,1-dioxide and a 4'-OP-phenyl/4'-OP-naphthyllithium compound to give the corresponding 3-(phenyl/naphthyl)-3-(4'-OP-1'-phenyl/4'-OP-1'-naphthyl)-2,3-dihydrobenz[d]isothiazole-1,1-dioxide wherein P represents a protecting group compatible with organometallic reagents. The compound thus prepared is then reacted with the selected carboxylic acid halide to give the corresponding 2-carbonyl derivative which is then treated with acid to remove the protecting group and yield the product. The phenyl or naphthyl group of the 3-(phenyl/naphthyl)-benz[d]isothiazole-1,1-dioxide employed in the initial step of the synthesis may be unsubstituted, or it may be substituted with, for example, an N-heterocyclic moiety and/or other substituents.

The present invention is concerned with certain 3-substituted-benz[d]isothiazole-1,1-dioxides useful as intermediates in the aforementioned synthesis.

SUMMARY OF THE INVENTION

It is, therefore, the primary object of the present invention to provide novel 3-substituted-benz[d]isothiazole-1,1-dioxides useful as intermediates in the synthesis of certain 3,3-disubstituted-2,3-dihydrobenz[d]isothiazole-1,1-dioxide dyes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

According to the present invention, 3-(phenyl/naphthyl)-benz[d]isothiazole-1,1-dioxides are provided wherein the 3-phenyl or 3-naphthyl group is substituted in the 4'-position with an N-heterocyclic moiety which compounds will be defined with greater particularity hereinafter.

For a fuller understanding of the nature and objects of the invention, reference should be had to the following detailed description.

DESCRIPTION OF THE PREFERRED EMBODIMENTS

Specifically, the compounds of the present invention may be represented by the formula:

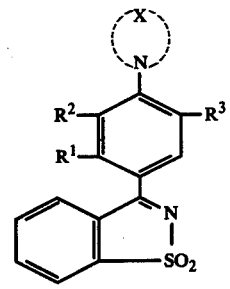

wherein $R^1$ and $R^2$ taken individually each are hydrogen, alkoxy or alkyl and taken together represent the carbon atoms necessary to complete a fused benzene ring, $R^3$ is hydrogen, alkoxy or alkyl and X represents the atoms necessary to complete piperidino, pyrrolidino, N-methylpiperazino, morpholino, thiomorpholino or tetrahydro-2H,4H-1,3,6-dioxazocino. Preferably, the alkyl groups and the alkoxy groups comprising $R^1$, $R^2$ and $R^3$ are lower alkyl having 1 to 4 carbon atoms and lower alkoxy having 1 to 4 carbon atoms. Usually, $R^1$ and $R^2$ are hydrogen or a fused benzene ring and $R^3$ is hydrogen.

Specific examples of compounds within the scope of the present invention are as follows:

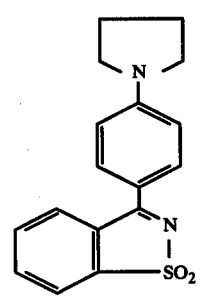

(1)

-continued
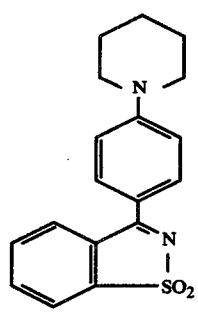
(2)
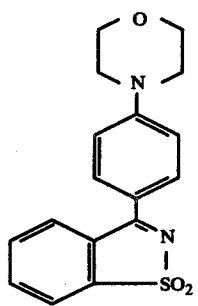
(3)
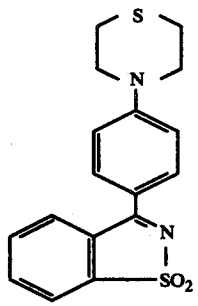
(4)
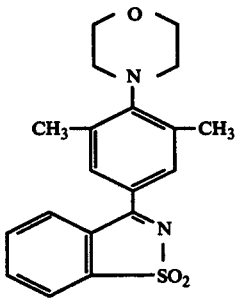
(5)
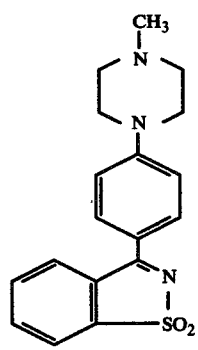
(6)
-continued
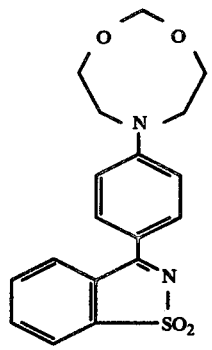
(7)
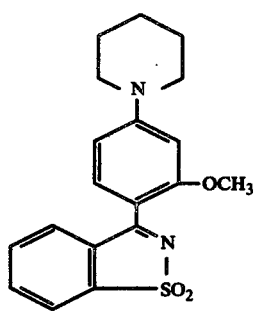
(8)
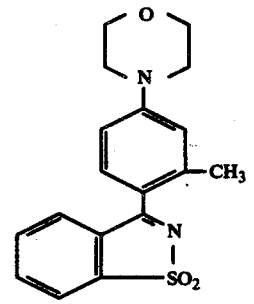
(9)
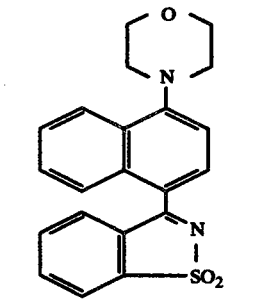
(10)
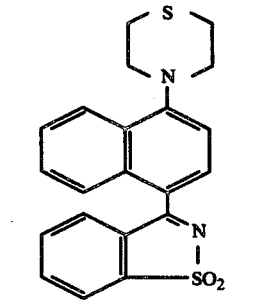
(11)

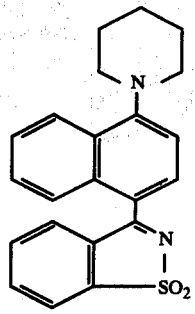

(12)

To prepare the compounds of the present invention, the selected N-(4-halophenyl/4-halonaphthyl) heterocyclic compound is converted to the corresponding 4-lithium derivative by reaction with n-butyllithium or lithium metal. The halo substituent may be chloro, bromo or iodo when lithium metal is employed and is either bromo or iodo when a lithium exchange reaction is employed. The lithium derivative is then reacted with the N-lithium salt of saccharin to yield the corresponding 3-substituted-benz[d]isothiazole-1,1-dioxide as illustrated in the following reaction sequence.

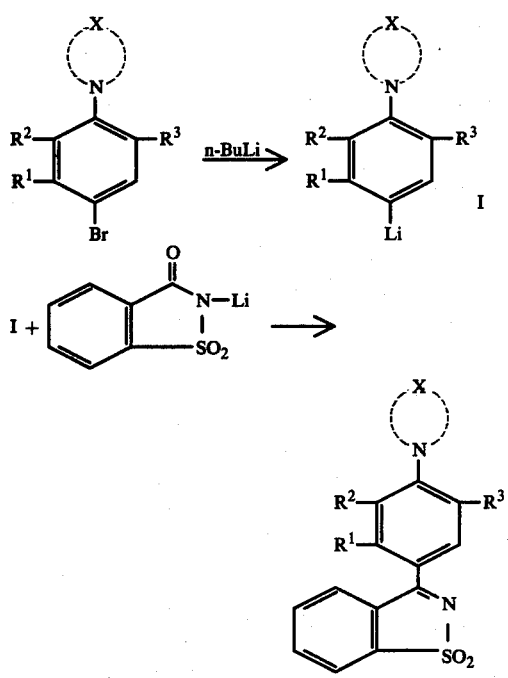

The subject compounds also may be prepared by reacting the selected N-(4-halophenyl/4-halonaphthyl) heterocyclic compound where halo is chloro, bromo or iodo with magnesium metal to form the corresponding Grignard derivative which is then reacted with saccharin pseudo-chloride.

The 4-halo derivatives may be prepared by reacting the N-(phenyl/naphthyl) heterocyclic compound with, for example, bromine or chlorine with or without a catalyst, N-bromosuccinimide or iodinemonochloride. Where the N-(phenyl/naphthyl)morpholines, thiomorpholines, N-methylpiperazines, piperidines and pyrrolidines are not commercially available, they may be prepared by reacting an aniline (or α-naphthylamine) with ClCH₂CH₂XCH₂CH₂Cl wherein X is —O—, —S—,

—CH₂— or a covalent bond, respectively. These compounds and their 4-halo derivatives also may be prepared by other procedures disclosed in the art. The N-(phenyl/naphthyl)tetrahydro-2H,4H-1,3,6-dioxazocines may be prepared by reacting N,N'-di(β-hydroxyethyl)anilines [or α-naphthyl-N,N'-di(β-hydroxyethyl amines)] or the 4-halo derivatives thereof with certain dihalomethanes in the presence of a solid alkali metal hydroxide or concentrated aqueous solution thereof and a quaternary ammonium salt. The dioxazocine compounds and their synthesis forms the subject matter of copending application Ser. No. 836,066 of Louis Cincotta, James W. Foley and Marcis M. Kampe filed concurrently herewith.

The following examples are given to illustrate the present invention and are not intended to limit the scope thereof.

EXAMPLE 1

Preparation of the compound of formula (3)

(a) 25 g. of N-phenylmorpholine was dissolved in 200 ml. of carbon tetrachloride and stirred well. To this was added all at once 27.2 g. of N-bromosuccinimide. There was an exotherm to 45° C. The reaction solution was stirred until the temperature began to decrease and then was heated to reflux for 3 hours. TLC on silica gel with 3/2 petroleum ether/ether indicated that the reaction was complete. The reaction solution was then cooled, the succinimide removed by filtration and the solution evaporated to yield a yellow solid. The solid was dissolved in 250 ml. of ethanol and cooled to give 22 g. of N-(p-bromophenyl)morpholine as white crystals.

(b) N-(p-bromophenyl)morpholine (30 g., 0.124 mol.) prepared as in step (a) was dissolved in 200 ml. of dry tetrahydrofuran under nitrogen and cooled to −60° C. to −70° C. To the resulting white slurry was added 2.4M n-butyllithium (51.6 ml., 0.124 mol.) while keeping the temperature below −60° C. After the addition was complete, the reaction mixture was stirred for 1 hour at −70° C. to −60° C.

(c) A tetrahydrofuran solution of the N-lithium salt of saccharin (0.124 mol.) was slowly added to the reaction mixture of step (b) through a double ended needle and the mixture was stirred for 1 hour at −70° C. to −60° C. The resulting pale gray slurry was allowed to come slowly to room temperature turning into a dark solution, then orange. The reaction mixture was poured into 150 ml. of water, the pH adjusted to about 6 and extracted with ethyl ether. The ether was partially evaporated and allowed to stand. 11.0 grams of yellow crystals were collected. The mother liquor was evaporated to give 9.8 g. of green solid which was dissolved in hot benzene containing a trace of toluenesulfonic acid. The solution was refluxed with a Dean-Stark trap for 2 hours. The benzene was evaporated and the solid washed with acetone to give 8.94 g. of yellow solid which was combined with the previously collected yellow crystals to give a total weight of 19.9 g. of the title compound.

The N-lithium salt of saccharin used in step (c) was prepared as follows:

Saccharin (22.7 g., 0.124 mol.) was dissolved in about 300 ml. of dry tetrahydrofuran under nitrogen and cooled to −65° C. n-Butyllithium (2.4M) was added dropwise until a persistent peach color occurred. The solution was stirred at −60° C to −65° C for 1 hour and then used directly in step (c) of the above example.

EXAMPLE 2

Preparation of the compound of formula (7)

The title compound was prepared according to the procedures described in steps (b) and (c) of Example 1 using N-(p-bromophenyl)tetrahydro-2H,4H-1,3,6-dioxazocine.

It will be appreciated that the 4-bromo and corresponding 4-lithium derivatives of N-(phenyl)thiomorpholine pyrrolidine, piperidine and N-methylpiperazine may be prepared according to the procedures set forth above and reacted with the N-lithium salt of saccharin in the same manner described in the Examples to yield the corresponding 3-substituted-benz[d]isothiazole-1,1-dioxides. Also, it will be appreciated that the naphthyl compounds of the present invention may be prepared similarly.

As mentioned above, the compounds of the present invention are useful as intermediates in the synthesis of certain 3,3-disubstituted-2,3-dihydrobenz[d]isothiazole-1,1-dioxides possessing a carbonyl group in the 2-position. Such compounds possessing a 4'-hydroxyphenyl moiety as one of the 3,3 substituents and a phenyl/naphthyl or 4'-substituted phenyl/4'-substituted naphthyl moiety as the other of the 3,3 substituents form the subject matter of copending U.S. patent application Ser. No. 836,021 of Stanley M. Bloom, Alan L. Borror and James W. Foley filed concurrently herewith and of copending U.S. patent application Ser. Nos. 835,998, 836,005 and 836,009 of Stanley M. Bloom, Alan L. Borror and James W. Foley also filed concurrently herewith. As discussed in the aforementioned applications, compounds may be selected for use as classical pH-sensitive indicator dyes or as photographic optical filter agents and filter agent precursors depending upon the 2-substituent of the benz[d]isothiazole ring. The photographic use of those compounds which may be employed as photographic optical filter agents and filter agent precursors forms the subject matter of copending U.S. patent application Ser. No. 836,006 of Stanley M. Bloom, Alan L. Borror and James W. Foley filed concurrently herewith. The 2,3-dihydrobenz[d]isothiazole-1,1-dioxides possessing a 4'-hydroxynaphthyl moiety as one of the 3,3 substituents and a naphthyl or 4'-substituted naphthyl moiety as the other of the 3,3 substituents form the subject matter of copending U.S. patent application Ser. No. 836,067 of Alan L. Borror, Louis Cincotta, Ernest W. Ellis and James W. Foley filed concurrently herewith, and as described therein, compounds may be selected for use as classical pH-sensitive indicator dyes or as antihalo dyes in photography.

The substitution of the 3-phenyl/naphthyl substituent of the aforementioned 3,3-disubstituted-2,3-dihydrobenz[d]isothiazole-1,1-dioxides with an N-heterocyclic moiety has been found advantageous for adjusting the spectral absorption characteristics of the dyes. For example, the optical transmission densities of 2-acetyl-3-(3',5'-dimethyl-4'-hydroxy-1'-phenyl)-3-(4'-R-1'-phenyl)-2,3-dihydrobenz[d]isothiazole-1,1-dioxides in aqueous potassium carbonate solution were measured on a logarithm scale over a wavelength range of 350 nm to 700 nm. Where R is pyrrolidino, the λ max is 597 nm, where R is morpholino, the λ max is 457 nm and where R is tetrahydro-2H,4H-1,3,6-dioxazocino, the λ max is 538 as compared to 562 nm for N,N-dimethylamino. Besides permitting adjustments toward the longer and shorter wavelengths, N-heterocyclic moieties also can be used to advantageously change the shape of the spectral curve. For example, where R is morpholino, the dye has a relatively broad absorption curve (W½h is 160 nm) and where R is pyrrolidino, the dye has a comparatively narrow absorption curve (W½h is 118 nm). "W½h" is defined as the width of the curve at ½ the height of the peak. Thus, depending upon its intended use, dyes can be prepared possessing relatively narrow to relatively broad absorption curves with a λ max at various wavelengths over a relatively broad wavelength range.

Since certain changes may be made in the above processes and products without departing from the scope of the invention herein involved, it is intended that all matter contained in the above description shall be interpreted as illustrative and not in a limiting sense.

What is claimed is:

1. A compound of the formula

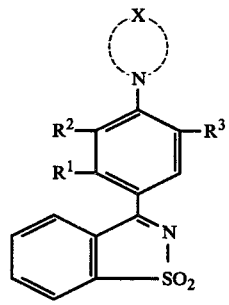

wherein $R^1$ and $R^2$ taken individually each are hydrogen, alkoxy having 1 to 4 carbon atoms or alkyl having 1 to 4 carbon atoms and taken together represent the carbon atoms necessary to complete a fused benzene ring, $R^3$ is hydrogen, alkoxy having 1 to 4 carbon atoms or alkyl having 1 to 4 carbon atoms and X represents the atoms necessary to complete piperidino, pyrrolidino, N-methylpiperazino, morpholino, thiomorpholino or tetrahydro-2H,4H-1,3,6-dioxazocino.

2. A compound as defined in claim 1 wherein X represents the atoms necessary to complete piperidino.

3. A compound as defined in claim 1 wherein X represents the atoms necessary to complete pyrrolidino.

4. A compound as defined in claim 1 wherein X represents the atoms necessary to complete N-methylpiperazino.

5. A compound as defined in claim 1 wherein X represents the atoms necessary to complete morpholino.

6. A compound as defined in claim 1 wherein X represents the atoms necessary to complete thiomorpholino.

7. A compound as defined in claim 1 wherein X represents the atoms necessary to complete tetrahydro-2H,4H-1,3,6-dioxazocino.

8. A compound as defined in claim 1 wherein $R^1$ and $R^2$ each are hydrogen.

9. A compound as defined in claim 1 wherein $R^1$ and $R^2$ taken together represent the carbon atoms necessary to complete a fused benzene ring.

10. A compound as defined in claim 8 wherein $R^3$ is hydrogen.

11. A compound as defined in claim 9 wherein $R^3$ is hydrogen.

12. A compound as defined in claim 10 wherein X represents the atoms necessary to complete morpholino.

13. A compound as defined in claim 10 wherein X represents the atoms necessary to complete tetrahydro-2H,4H-1,3,6-dioxazocino.

* * * * *